(12) United States Patent
Tsai et al.

(10) Patent No.: US 9,505,851 B2
(45) Date of Patent: Nov. 29, 2016

(54) ANTIFUNGAL COMPOSITE AND METHOD FOR MANUFACTURING THE SAME

(71) Applicant: Ting-Hung Su, Taipei (TW)

(72) Inventors: Tsung-Lin Tsai, Tainan (TW); Chia-Cheng Ho, Kaohsiung (TW); Hao-Chen Wang, Tainan (TW); Ting-Hung Su, Taipei (TW)

(73) Assignee: Ting-Hung Su, Taipei (TW)

( * ) Notice: Subject to any disclaimer, the term of this patent is extended or adjusted under 35 U.S.C. 154(b) by 0 days.

(21) Appl. No.: 14/642,258

(22) Filed: Mar. 9, 2015

(65) Prior Publication Data
US 2016/0021876 A1   Jan. 28, 2016

(30) Foreign Application Priority Data
Jul. 22, 2014   (TW) .............................. 103125167 A

(51) Int. Cl.
| A01N 25/22 | (2006.01) |
| A01N 43/16 | (2006.01) |
| C08B 37/16 | (2006.01) |
| C08J 5/18 | (2006.01) |
| A01N 25/10 | (2006.01) |
| A01N 25/34 | (2006.01) |

(52) U.S. Cl.
CPC ........... *C08B 37/0015* (2013.01); *A01N 25/10* (2013.01); *A01N 25/34* (2013.01); *C08J 5/18* (2013.01); *C08J 2303/04* (2013.01); *C08J 2367/02* (2013.01)

(58) Field of Classification Search
None
See application file for complete search history.

(56) References Cited

U.S. PATENT DOCUMENTS

| 4,539,399 A * | 9/1985 | Armstrong ......... B01D 15/3833 210/502.1 |
| 4,727,064 A * | 2/1988 | Pitha .................... A61K 31/565 106/205.01 |
| 5,134,127 A * | 7/1992 | Stella ............... A61K 47/48969 514/58 |
| 5,728,823 A * | 3/1998 | Reuscher ............. B01D 69/141 536/103 |
| 2003/0017263 A1* | 1/2003 | Washizu ................ B82Y 30/00 427/162 |
| 2004/0136643 A1* | 7/2004 | Washizu ................ G01N 21/45 385/16 |
| 2005/0226661 A1* | 10/2005 | Ohmura ............ G03G 9/09708 399/333 |
| 2008/0220054 A1* | 9/2008 | Shastri .................. A61K 47/34 424/443 |
| 2011/0129937 A1* | 6/2011 | Naaman ............... G01N 27/126 436/93 |

FOREIGN PATENT DOCUMENTS

| CN | 101837465 B | 11/2011 |
| CN | 103159983 A | 6/2013 |
| CN | 103172892 A | 6/2013 |
| WO | WO 0062793 A2 * | 10/2000 ........... A61K 9/0019 |

* cited by examiner

*Primary Examiner* — Peter A Salamon
(74) *Attorney, Agent, or Firm* — Chun-Ming Shih; HDLS IPR Services

(57) ABSTRACT

The invention provides an antifungal composite comprising an antifungal agent and β-cyclodextrin surface-modified with a long carbon chain compound, wherein the antifungal agent is clad in β-cyclodextrin surface-modified with a long carbon chain compound as a carrier, and thus a use of inhibiting harmful fungi can be provided by sustained release of the antifungal agent from the composite. The antifungal composite may be retained on the surface of the resin materials to increase the concentration of the antifungal composite on the surface of the resin materials by adjusting the difference of the lipophilic and hydrophilic characters between the antifungal composite and the resin materials, and thus an antifungal effect can be increased. The invention also relates to a method for manufacturing an antifungal composite.

1 Claim, 4 Drawing Sheets

--- solving β-cyclodextrin and an antifungal agent in a solvent by molar ratio of 1:1-10:1 — S150

↓ mixing and carrying out a reaction of β-cyclodextrin and the antifungal agent for 1 hour to 2 hours to obtain a mixture — S160

↓ drying the mixture to obtain an antifungal composite with the antifungal agent clad in β-cyclodextrin — S170

US 9,505,851 B2

ANTIFUNGAL COMPOSITE AND METHOD FOR MANUFACTURING THE SAME

BACKGROUND OF THE INVENTION

Field of the Invention

The invention relates to an antifungal composite, particularly an antifungal composite comprising an antifungal agent and β-cyclodextrin surface-modified with a long carbon chain compound, wherein the antifungal agent is clad in β-cyclodextrin, and the antifungal composite may be used in a resin sheet to enhance the antifungal effect.

Description of the Related Art

β-cyclodextrin is a cyclic oligosaccharide of seven glucopyranose units consisting of (α-1,4)-linked α-D-glucopyranose units. β-cyclodextrin is white crystalline powder, odourless, slightly sweet, and can be dissolved in water, melting point between 290-305° C. β-cyclodextrin contains a lipophilic central cavity and a hydrophilic outer surface, which has been estimated to be similar to character of a surfactant, and has a emulsification for water and oil materials. The central cavity has hydrogen atoms and ethereal oxygens of the glucose residues, which gives it a lipophilic or nonpolar character. β-cyclodextrin can form composites with various compounds, e.g. antifungal agents. In these composites, β-cyclodextrin are mainly used to increase stability, solubility, sustained release of inclusion, emulsification, anti-oxidation, anti-decomposition, heat retaining, moisture-proof and have the effect of shielding odors. Therefore, β-cyclodextrin can be used in antifungal package materials for food products.

At present, there are two methods of β-cyclodextrin using in antifungal package materials for food products. One forms a composite by β-cyclodextrin and an antifungal agent firstly, and then the composite is added to a food product package material, e.g. resin material to form an antifungal resin sheet. The antifungal effect can be produced by sustained release and migration of the antifungal agent from the composite. Another carries β-cyclodextrin on fiber package materials firstly, and an antifungal agent is clad in β-cyclodextrin. The antifungal effect can be produced by sustained release of the antifungal agent.

The antifungal effect may be produced only when the antifungal agent contacts with thallus. However, as the antifungal composite mixes with the resin material, the release of the antifungal agent of the antifungal composite somewhat may be shielded. Therefore, it can enhance the antifungal effect by increasing the surface contact area of the antifungal composite. It has been found there is not any existed publication relating to a product, e.g. an antifungal resin sheet manufacturing by an antifungal composite comprising an antifungal agent and β-cyclodextrin surface-modified with a long carbon chain compound, wherein the antifungal agent is clad in β-cyclodextrin.

SUMMARY OF THE INVENTION

One object of the present invention is to provide an antifungal composite comprising an antifungal agent and β-cyclodextrin, wherein the antifungal agent, e.g. cinnamaldehyde is clad in β-cyclodextrin as a carrier, the weight ratio of β-cyclodextrin/the antifungal agent is from 1 to 10, and thus a use of inhibiting harmful fungi can be provided by sustained release of the antifungal agent from the composite. Also, an excellent antifungal effect can be achieved by only a small amount of the antifungal agent.

Another object of the present invention is to provide an antifungal composite comprising an antifungal agent and β-cyclodextrin surface-modified with a long carbon chain compound, wherein the antifungal agent is clad in β-cyclodextrin surface-modified with a long carbon chain compound as a carrier, and thus a use of inhibiting harmful fungi can be provided by sustained release of the antifungal agent from the composite. The antifungal composite may be retained on the surface of the resin materials to increase the concentration of the antifungal composite on the surface of the resin materials by adjusting the difference of the lipophilic and hydrophilic characters between the antifungal composite and the resin materials, and thus an antifungal effect can be increased.

Another object of the present invention is to provide a method for manufacturing an antifungal resin sheet, which is a chemical process. The method comprises steps: (a) adding a resin material in a solvent; (b) solving the resin material in the solvent to form a solution containing the resin material by heating at a temperature between 70° C. and 300° C. (c) adding and mixing 0.01 wt % to 70 wt % of an antifungal composite in the solution, and then stop heating and cooling to room temperature to obtain a mixture; and (d) removing the solvent, exhausting solvent for a period of time to assist removing the solvent during removing the solvent and molding the mixture to be an antifungal resin sheet.

Specifically, the solvent is selected from a group consisting of ammonia solution, 6-aminocaproic acid, dimethyl formamide (DMF), dimethyl acetamide (DMAc), methyl ethyl ketone (MEK), formic acid, xylene and toluene. In an aspect, it is suitable to use toluene as the solvent and heating temperature between 80° C. and 120° C. of step (b) as the resin material of step (a) is polyethylene resin. In another aspect, it is suitable to use formic acid as the solvent and heating temperature between 100° C. and 120° C. of step (b) as the resin material of step (a) is polyamide (nylon). In addition, the invention relates to an antifungal resin sheet manufactured by the above method of the chemical process comprising mixing a resin material and an antifungal agent.

Another object of the present invention is to provide a method for manufacturing an antifungal resin sheet, which is a physically calendaring process. The method comprises steps: (a) calendaring a resin material and an antifungal composite to form a mixture; and (b) molding the mixture to be an antifungal resin sheet. The step (a) further comprises mixing a resin material and the antifungal composite before calendaring. Alternatively, the step (a) further comprises pre-melting a resin material followed by adding the antifungal composite before calendaring. Specifically, the resin material may be polyethylene terephthalate (PET) or polyamide (nylon). In addition, the invention relates to an antifungal resin sheet manufactured by the above method of the physically calendaring process comprising mixing a resin material and an antifungal agent.

DESCRIPTION OF THE EMBODIMENTS

The features of the invention believed to be novel are set forth with particularity in the appended claims. The invention itself, however, may be best understood by reference to the following detailed description of the invention, which describes an exemplary embodiment of the invention, taken in conjunction with the accompanying drawings, in which:

An embodiment of the invention relates to an antifungal composite comprising an antifungal agent and β-cyclodextrin, wherein the antifungal agent, e.g. cinnamaldehyde is clad in β-cyclodextrin as a carrier, the weight ratio of β-cyclodextrin/the antifungal agent is from 1 to 10, and thus a use of inhibiting harmful fungi can be provided by sustained release of the antifungal agent from the composite. Also, an excellent antifungal effect can be achieved by only a small amount of the antifungal agent.

Another embodiment of the invention relates to an antifungal composite comprising an antifungal agent and β-cyclodextrin surface-modified with a long carbon chain compound, wherein the antifungal agent is clad in β-cyclodextrin surface-modified with a long carbon chain compound as a carrier, and thus a use of inhibiting harmful fungi can be provided by sustained release of the antifungal agent from the composite. The antifungal composite may be retained on the surface of the resin materials to increase the concentration of the antifungal composite on the surface of the resin materials by adjusting the difference of the lipophilic and hydrophilic characters between the antifungal composite and the resin materials, and thus an antifungal effect can be increased. In an embodiment, the long carbon chain compound has 6-18 carbon atoms. The long carbon chain compound may be dodecyl trimethoxy silane, octadecyl trimethoxysilane, n-octyl triethoxy silane, methyl trimethoxy silane, methyl ethyl silane or sodium dodecyl benzene sulfonate.

Figure 1:
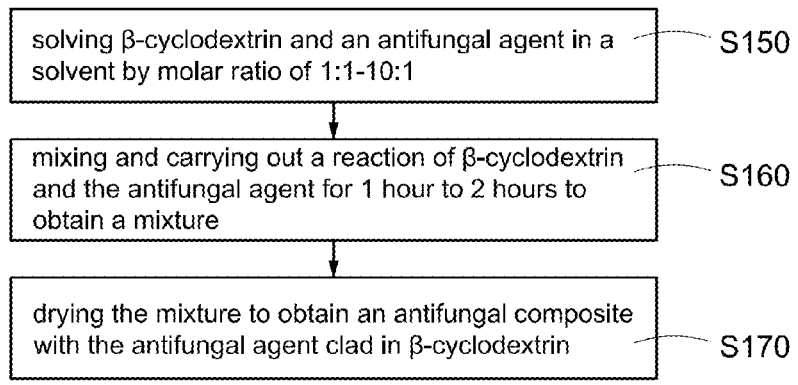
FIG. 1 shows a flow chart of steps of a method for manufacturing an antifungal composite of an embodiment according to the invention.

Detailed description of a method for manufacturing an antifungal composite of the invention is described as follow. Please refer to FIG. 1. A method for manufacturing the antifungal composite comprises steps: step S150, solving β-cyclodextrin and an antifungal agent in a solvent by molar ratio of 1:1-10:1; step S160, mixing and carrying out a reaction of β-cyclodextrin and the antifungal agent for 1 hour to 2 hours to obtain a mixture; and step S170, drying the mixture to obtain an antifungal composite with the antifungal agent clad in β-cyclodextrin. In an embodiment of step S150, β-cyclodextrin as a carrier and the lipophilic antifungal agent, e.g. cinnamaldehyde are solved in water by heating at a temperature between 80° C. and 90° C. by molar ratio of 1:1-10:1. In another embodiment of step S150, β-cyclodextrin as a carrier and the lipophilic antifungal agent, e.g. cinnamaldehyde are solved in an organic solvent, for example dichloromethane or dimethyl sulfoxide (DMSO) by molar ratio of 1:1-10:1.

Figure 2:
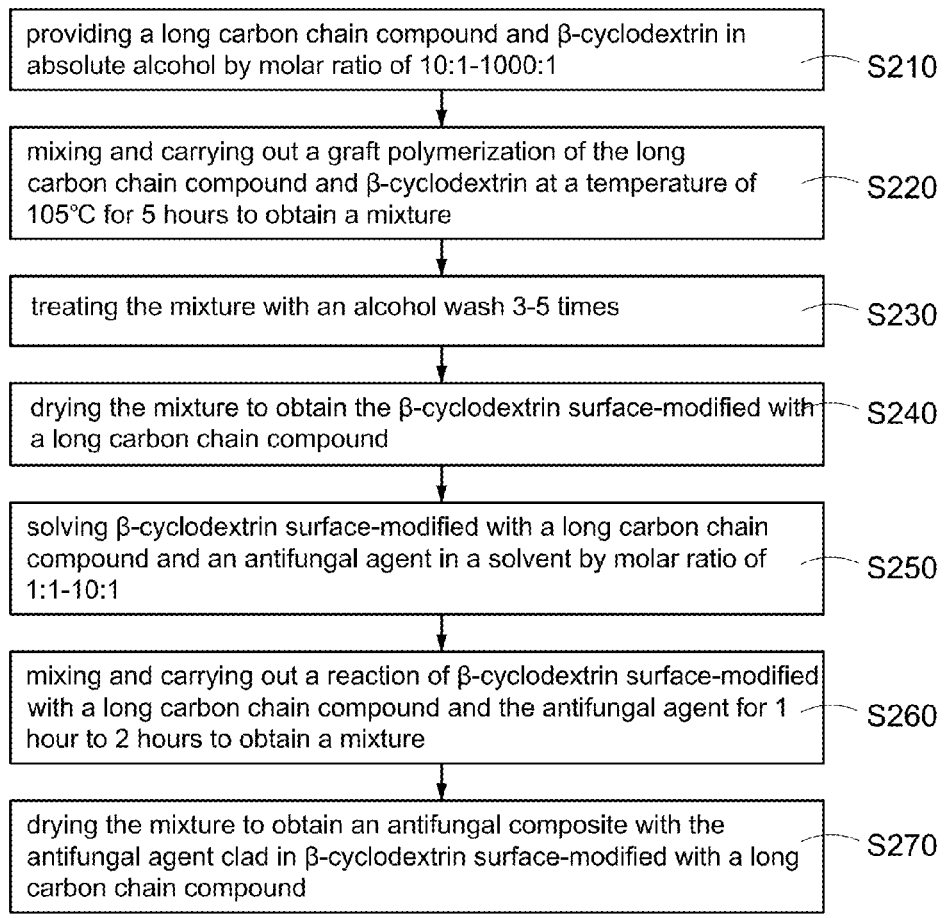
FIG. 2 shows a flow chart of steps of a method for manufacturing an antifungal composite with surface-modification with a long carbon chain compound of an embodiment according to the invention.

Next, another method for manufacturing an antifungal composite of the invention is described as follow. The difference to the above method is that β-cyclodextrin of the present method is surface-modified with a long carbon chain compound. Please refer to FIG. 2. At first, a method for grafting a long carbon chain compound to the surface of β-cyclodextrin comprises steps of S210 to S240: step S210, providing a long carbon chain compound and β-cyclodextrin in absolute alcohol by molar ratio of 10:1-1000:1, wherein the long carbon chain compound may be dodecyltrimethoxysilane; step S220, mixing and carrying out a graft polymerization of the long carbon chain compound and β-cyclodextrin at room temperature for 18 hours or a temperature of 105° C. for 5 hours to obtain a mixture; step S230, treating the mixture with an alcohol wash 3-5 times; and step S240, drying the mixture to obtain the β-cyclodextrin surface-modified with a long carbon chain compound.

Next, step S250 is carried out by solving β-cyclodextrin surface-modified with a long carbon chain compound and an antifungal agent in a solvent by molar ratio of 1:1-10:1; step S260 is carried out by mixing and carrying out a reaction of β-cyclodextrin surface-modified with a long carbon chain compound and the antifungal agent for 1 hour to 2 hours to obtain a mixture; and step S270 is carried out by drying the mixture to obtain an antifungal composite with the antifungal agent clad in β-cyclodextrin surface-modified with a long carbon chain compound. In an embodiment of step S250, β-cyclodextrin surface-modified with a long carbon chain compound as a carrier and the lipophilic antifungal agent, e.g. cinnamaldehyde are solved in water by heating at a temperature between 80° C. and 90° C. by molar ratio of 1:1-10:1. In another embodiment of step S250, β-cyclodextrin surface-modified with a long carbon chain compound as a carrier and the lipophilic antifungal agent, e.g. cinnamaldehyde are solved in an organic solvent, for example dichloromethane or dimethyl sulfoxide (DMSO) by molar ratio of 1:1-10:1.

In an embodiment, an antifungal composite manufactured by the above methods may be calendared with resin materials such as polyethylene (PE), polypropylene (PP), polyamide (nylon) or polyethylene terephthalate (PET) to produce mother particles with a high concentration (3%~10%). The mother particles can be used to produce an antifungal resin product by adjusting to an effective antifungal concentration (0.1%~3%).

Detailed description of a method for manufacturing an antifungal resin sheet of the invention is described as follow. In an embodiment, a method for manufacturing an antifungal resin sheet, which is a chemical process, is provided. At first, a resin material is added and solved in an organic solvent such as a solvent is selected from a group consisting of ammonia solution, 6-aminocaproic acid, dimethyl formamide (DMF), dimethyl acetamide (DMAc), methyl ethyl ketone (MEK), formic acid, xylene and toluene to form a solution. Next, an antifungal composite is added in the solution to obtain a mixture. Finally, the solvent is removed and the mixture is molded to be an antifungal resin sheet. In the embodiment, a resin material such as polyethylene (PE) or polyamide (nylon) may be used.

In an embodiment, a method for manufacturing an antifungal PE resin sheet having the antifungal composite comprises steps: (a) a PE resin is added in toluene; (b) PE resin is solved sufficiently in toluene to form a solution containing PE by heating at a temperature between 80° C. and 120° C.; (c) 0.5 wt % to 10 wt % of an antifungal composite is added in the solution to obtain a mixture, and then stop heating and cooling to room temperature to obtain a mixture; and (d) toluene is removed, toluene may be exhausted for a period of time to assist removing toluene during removing toluene and molding the mixture to be an antifungal resin sheet.

In another embodiment, a method for manufacturing an antifungal nylon resin sheet having the antifungal composite comprises steps: (a) a nylon resin is added in formic acid; (b) nylon resin is solved sufficiently in formic acid to form a solution containing nylon resin by heating at a temperature between 100° C. and 120° C.; (c) 0.5 wt % to 10 wt % of an antifungal composite is added in the solution to obtain a mixture, and then stop heating and cooling to room temperature to obtain a mixture; and (d) formic acid is removed, formic acid may be exhausted for a period of time to assist removing formic acid during removing formic acid and molding the mixture to be an antifungal resin sheet.

In another embodiment, a method for manufacturing an antifungal resin sheet, which is a physically calendaring process, is provided. The method comprises steps: (a) calendaring a resin material and an antifungal composite to form a mixture; and (b) molding the mixture to be an antifungal resin sheet. The step (a) further comprises mixing a resin material and the antifungal composite before calendaring. Alternatively, the step (a) further comprises pre-melting a resin material followed by adding the antifungal composite before calendaring. Specifically, the resin material may be polyethylene terephthalate (PET) or polyamide (nylon). In addition, the invention relates to an antifungal resin sheet manufactured by the above method of the physically calendaring process comprising mixing a resin material and an antifungal agent.

Figure 3A:
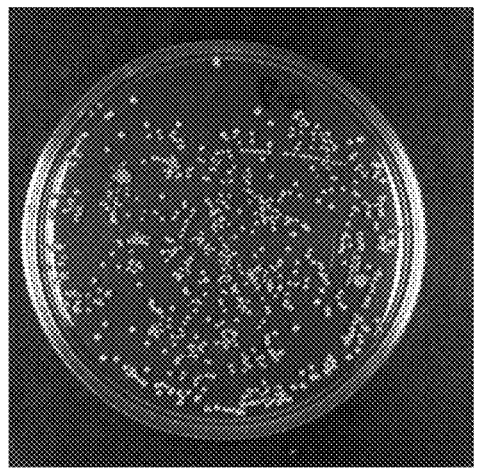
FIG. 3A shows an antifungal effect of a normal PET cloth for *staphylococcus aureus*.
Figure 3B:
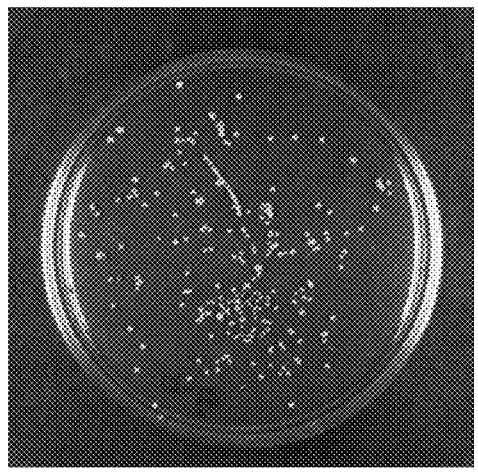
FIG. 3B shows an antifungal effect of PET cloth having antifungal composite without surface-modification with a long carbon chain compound for *staphylococcus aureus*.
Figure 4A:
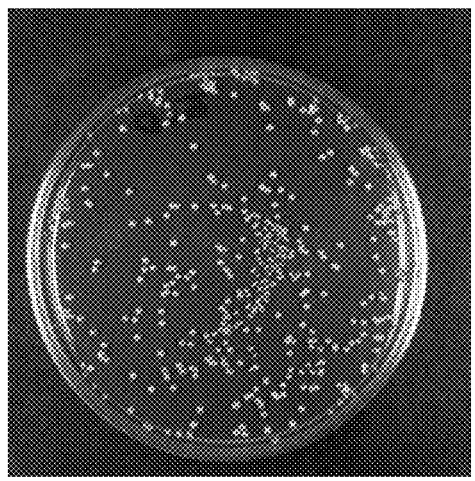
FIG. 4A shows an antifungal effect of a normal PET cloth for *E. coli*.
Figure 4B:
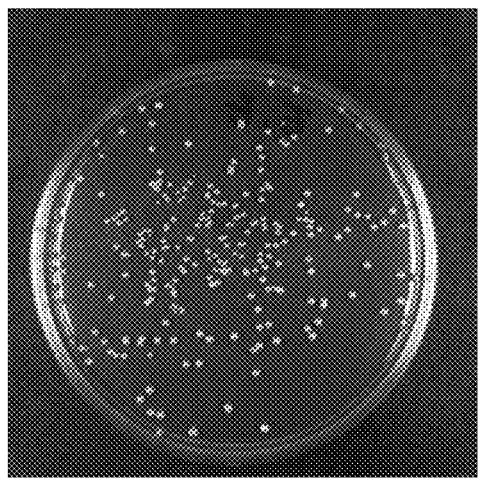
FIG. 4B shows an antifungal effect of PET cloth having antifungal composite without surface-modification with a long carbon chain compound for *E. coli*.
Figure 5A:
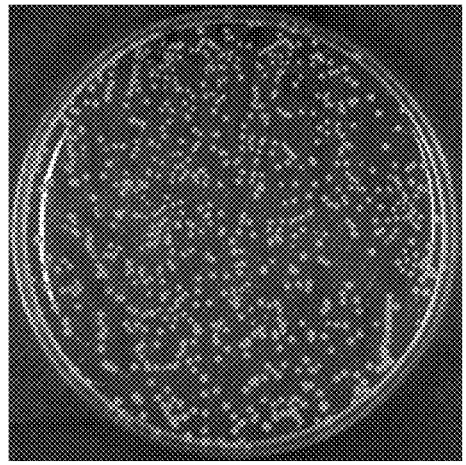
FIG. 5A shows an antifungal effect of a normal PET cloth for *staphylococcus aureus*.
Figure 5B:
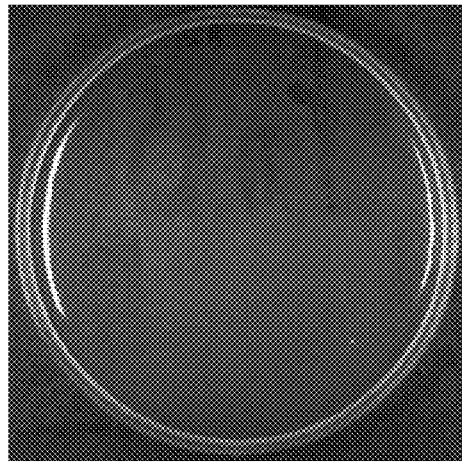
FIG. 5B shows an antifungal effect of PET cloth having antifungal composite with surface-modification with a long carbon chain compound for *staphylococcus aureus*.
Figure 6A:
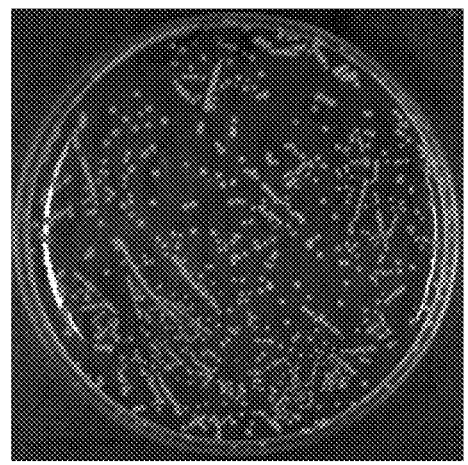
FIG. 6A shows an antifungal effect of a normal PET cloth for *E. coli*.
Figure 6B:
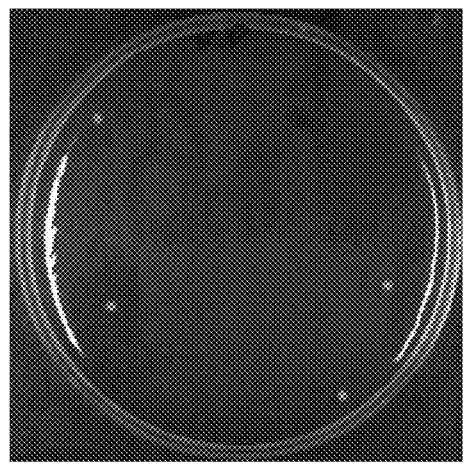
FIG. 6B shows an antifungal effect of PET cloth having antifungal composite with surface-modification with a long carbon chain compound for *E. coli*.

Please refer to FIGS. 3A to 6B. FIG. 3A shows an antifungal effect of a normal PET cloth for *staphylococcus aureus*; and FIG. 3B shows an antifungal effect of PET cloth having antifungal composite without surface-modification with a long carbon chain compound for *staphylococcus aureus*. Also, FIG. 4A shows an antifungal effect of a normal PET cloth for *E. coli*; and FIG. 4B shows an antifungal effect of PET cloth having antifungal composite without surface-modification with a long carbon chain compound for *E. coli*. In addition, FIG. 5A shows an antifungal effect of a normal PET cloth for *staphylococcus aureus*; and FIG. 5B shows an antifungal effect of PET cloth having antifungal composite with surface-modification with a long carbon chain compound for *staphylococcus aureus*. Also, FIG. 6A shows an antifungal effect of a normal PET cloth for *E. coli*; and FIG. 6B shows an antifungal effect of PET cloth having antifungal composite with surface-modification with a long carbon chain compound for *E. coli*.

Figure 7:
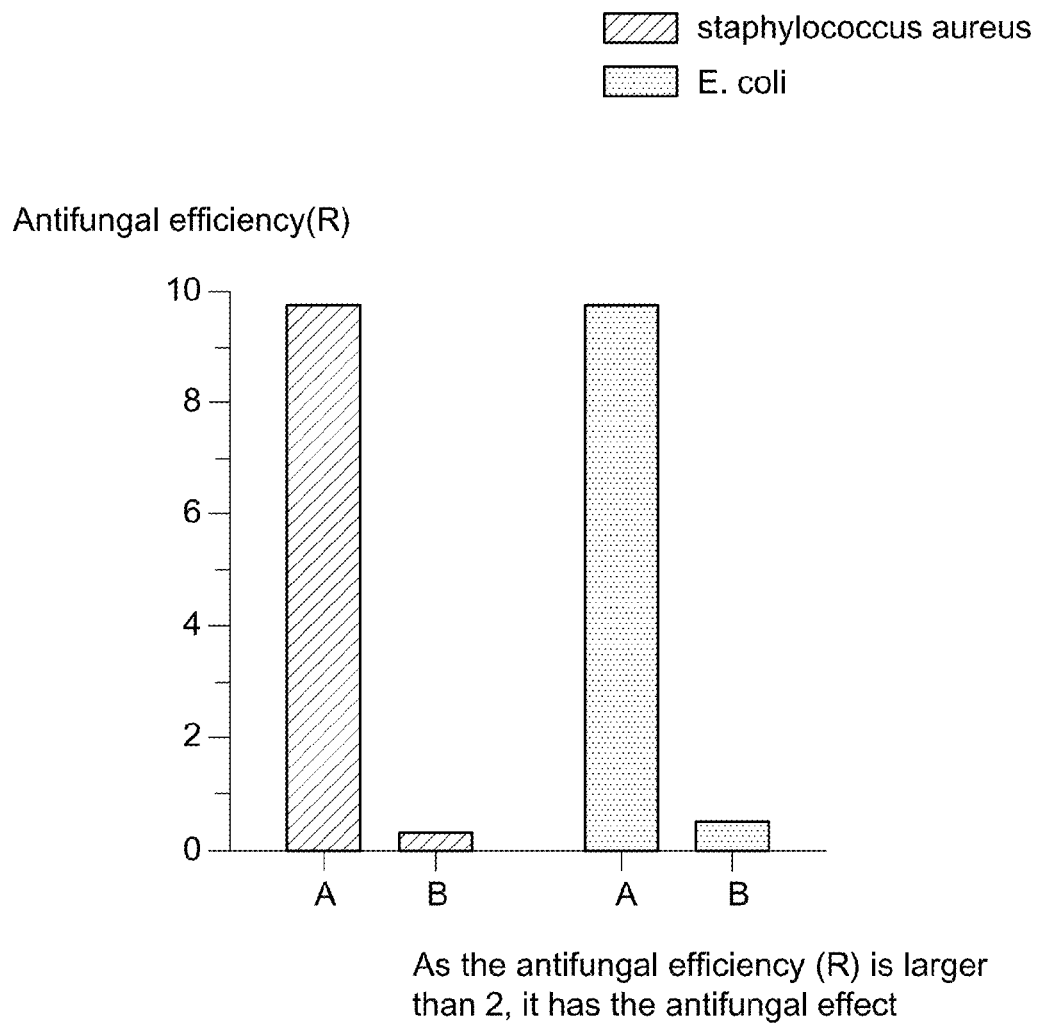
FIG. 7 is a bar chart in proportion showing an antifungal efficiency (R) of PET cloth having antifungal composite.

In an embodiment, PET resin having antifungal composite without surface-modification with a long carbon chain compound and PET resin having antifungal composite with surface-modification with a long carbon chain compound may be calendared to produce mother particles respectively, and then the mother particles can be used to produce an antifungal PET cloth by different weight. A test of an antifungal effect of PET cloth having antifungal composite is listed in Table 1 as below. In addition, FIG. 7 is a bar chart in proportion showing an antifungal efficiency (R) of PET cloth having antifungal composite, wherein A set represents PET resin having antifungal composite with surface-modification with a long carbon chain compound, and B set represents PET resin having antifungal composite without surface-modification with a long carbon chain compound. As the antifungal efficiency (R) is larger than 2, it has the antifungal effect.

TABLE 1

| | | germ | |
|---|---|---|---|
| | | *staphylococcus aureus* | *E. coli* |
| PET cloth having antifungal composite without surface-modification with a long carbon chain compound | blank set operation set | A large number A lesser degree | A large number A lesser degree |
| PET cloth having antifungal composite with surface-modification with a long carbon chain compound | blank set operation set | A large number A very small amount | A large number A very small amount |

The resin materials mixing with the antifungal composite of the invention can be used to produce resin products having the antifungal effect for food, building or medical application. Particularly, the invention provides an antifungal composite comprising an antifungal agent and β-cyclodextrin surface-modified with a long carbon chain compound, wherein the antifungal agent is clad in β-cyclodextrin surface-modified with a long carbon chain compound as a carrier, and thus a use of inhibiting harmful fungi can be provided by sustained release of the antifungal agent from the composite. The antifungal composite may be retained on the surface of the resin materials to increase the concentration of the antifungal composite on the surface of the resin materials by adjusting the difference of the lipophilic and hydrophilic characters between the antifungal composite and the resin materials, and thus an antifungal effect can be increased.

As the skilled person will appreciate, various changes and modifications can be made to the described embodiments. It is intended to include all such variations, modifications and equivalents which fall within the scope of the invention, as defined in the accompanying claims.

What is claimed is:

1. An antifungal composite comprising an antifungal agent and β-cyclodextrin, wherein the antifungal agent is clad in β-cyclodextrin, the weight ratio of β-cyclodextrin/the antifungal agent is from 1 to 10, and the β-cyclodextrin is surface-modified with a long carbon chain compound;

wherein the long carbon chain compound is Sodium dodecyl benzene sulfonate.

\* \* \* \* \*